United States Patent [19]

Dowd et al.

[11] Patent Number: 5,281,609
[45] Date of Patent: Jan. 25, 1994

[54] LEPORIN A, AN ANTIINSECTAN FUNGAL METABOLITE

[75] Inventors: Patrick F. Dowd; Donald T. Wicklow, both of Peoria, Ill.; James B. Gloer, Iowa City; Mark R. TePaske, Charles City, both of Iowa

[73] Assignees: The United States of America, as represented by the Secretary of Agriculture, Washington, D.C.; University of Iowa Research Foundation, Iowa City, Iowa

[21] Appl. No.: 950,346

[22] Filed: Sep. 24, 1992

[51] Int. Cl.$^5$ .................. C07D 491/052; A61K 31/44
[52] U.S. Cl. ........................................ 514/291; 546/89
[58] Field of Search .......................... 546/89; 514/291

[56] References Cited

U.S. PATENT DOCUMENTS 4,973,601  11/1990  Dowd et al. .................... 514/410
5,017,598   5/1991  Dowd et al. .................... 514/415

OTHER PUBLICATIONS

Wicklow, D. T., Mycologia, 77(4) 1985, pp. 531-534.
States and Christensen: Aspergillus, Mycologia, vol. 58, 1966, pp. 738-742.
TePaske et al. Tet. Lett. 32(41), pp. 5687-5690, 1991.
Gloer, James B., et al., "Antiinsectan Aflavinine Derivatives from the Sclerotia of *Aspergillus flavus*", *J. Org. Chem.*, 1988, 53, pp. 5457-5460.
Wicklow, Donald T., et al., "Sclerotial metabolites of *Aspergillus flavus* Toxic to a Detritivorous Maize Insect (*Carpophilus hemipterus, nitidulidae*)", *Trans. Br., Mycol. Soc.*, 91 (3), 1988, pp. 433-438.
Samson, Robert A., et al., "Typification of the Species of Aspergillus and Associated Telemorphs", *Advances in Penicillium and Aspergillus Systematics*, Plenum Press, N.Y., 1985, pp. 31-54.
American Type Culture Collection Catalogue of Fungi/Yeasts Seventeenth Edition, 1987, Jong, S. C. & Gant, M. J., editors, pp. 31-54.

*Primary Examiner*—C. Warren Ivy
*Assistant Examiner*—Phyllis G. Spivack
*Attorney, Agent, or Firm*—M. Howard Silverstein; John D. Fado; Randall E. Deck

[57] ABSTRACT

A novel N-methoxy-2-pyridone designated leporin A has been isolated from the sclerotia of the fungus, *Aspergillus leporis*. Leporin A is characterized by the structural formula

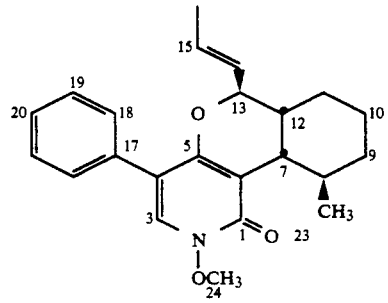

and is effective for controlling Lepidopteran insect pests.

5 Claims, No Drawings

LEPORIN A, AN ANTIINSECTAN FUNGAL METABOLITE

BACKGROUND OF THE INVENTION

1. Field of the Invention

This invention relates to a novel N-alkoxypyridone compound and its use as an insecticide for control of Lepidoptera species.

2. Description of the Prior Art

Toxic metabolites of fungi are thought to serve as chemical defense systems for the fungi that produce them, and may also be of use in protecting the food source from consumption by other organisms [see: Wicklow, In Toxigenic Fungi—Their Toxins and Health Hazards, H. Kurata et al. (ed.), Elsevier, N.Y., pp. 78–86 (1984)]. Dowd et al. [U.S. Pat. No. 4,973,601] disclosed that the class of fungal metabolites known as tremorgenic mycotoxins is toxic to insect species.

Many fungi produce specially adapted morphological structures called sclerotia that are critical to the long-term survival and propagation of the species [Willets, Biol. Rev. Cambridge Philos. Soc. 46: 387 (1971); Gloer et al., J. Org. Chem. 53: 5457–5460 (1988); Wicklow et al., Trans. Br. Mycol. Soc. 91: 433 (1988)]. The factors which permit the long-term survival of sclerotia in soil are not fully understood. Many vascular plants are known to selectively allocate metabolites to important physiological structures as chemical defenses against herbivory [Herbivores: Their Interaction with Secondary Plant Metabolites, G. Rosenthal et al. (ed.), Academic, N.Y., (1979)]. By analogy, it has been suggested that fungal sclerotia may have evolved chemical defenses against predation by fungivorous insects which commonly encounter sclerotia in soil [Wicklow et al., supra (1988); Wicklow et al., Can. J. Bot. 60: 525 (1982)]. However, aside from the sclerotia (ergot) of Claviceps spp. (which produce the ergot alkaloids), sclerotia have not been commonly explored for the production of unique, biologically active secondary metabolites. Gloer et al. [supra] and Wicklow et al. [supra (1988)] reported the isolation of four antiinsectan aflavinine derivatives that are selectively allocated to the sclerotia of *Aspergillus flavus* in concentrations effective against insects that encounter sclerotia under natural conditions. Dowd et al. (U.S. Pat. No. 5,017,598, issued May 21, 1991), also disclosed the isolation of an indole diterpene compound, nominine, having insecticidal activity, from the sclerotia of *Aspergillus nomius*.

SUMMARY OF THE INVENTION

We have now discovered a novel N-alkoxypyridone compound which has significant antiinsectan activity. This compound, which is produced in sclerotia of the fungus *Aspergillus leporis*, has been given the name leporin A. It has been organic solvent-extracted from the sclerotia and isolated in pure form by high-performance liquid chromatography (HPLC); its structure has been determined instrumentally. Leporin A is a previously unreported structure and is characterized by the following formula:

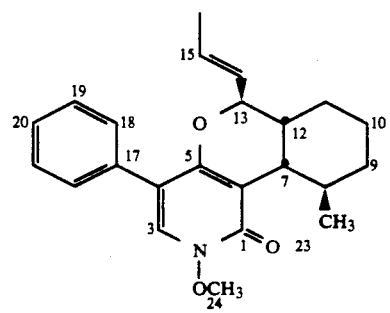

In accordance with this discovery, it is an object of the invention to introduce leporin A as a novel chemical compound having antiinsectan activity.

It is also an object of the invention to provide new compositions for controlling insects.

Another object of the invention is to provide an insecticide that is generated from natural renewable resources.

Other objects and advantages of this invention will become readily apparent from the ensuing description.

DETAILED DESCRIPTION OF THE INVENTION

A strain of the fungus, *A. leporis*, useful in producing leporin a in accordance with the invention has been deposited under the Budapest Treaty in the Agricultural Research Service Culture Collection in Peoria, Ill., and has been assigned Deposit No. NRRL 18990. This strain of *Aspergillus leporis* has been characterized by States and Christensen [Mycologia, 1966, 58:738] and Wicklow [Mycologia, 1985, 77:531], the contents of each of which are incorporated by reference herein.

As described by States and Christensen, *A. leporis* is characterized by compactly columnar conidial heads, sterigmata commonly biseriate in arrangement, and sclerotia which are dark colored, vertically elongate, and often irregular.

Colonies on Czapek's solution agar growing rapidly at room temperature (24°–26° C.), attaining a diameter of 4–6 cm in 10–12 days, plane or slightly wrinkled, floccose, white becoming ecru-olive to buffy olive with development of conidial structures, these sparse, most abundant centrally; sclerotia developing on the surface of the felt at 6–8 days, at first appearing as white masses near 1 mm in diam, later becoming black with white apices, conspicuous and abundant; reverse uncolored to pale yellow; odor not pronounced; exudate colorless, characteristic on developing sclerotia. Conidial heads at first globose then commonly becoming tight single columns deciduous as a unit, cylindrical 70–150$\mu$ wide or conical with apex flared to near 270$\mu$, occasionally split into divergent segments, up to 1 mm long in old cultures; conidiophores extremely variable in length, up to 2.5 mm by 6.5–13.0$\mu$ when arising from submerged hyphae, commonly 140–820$\mu$ long when borne from aerial hyphae, stalks mostly nonseptate, walls uniformly yellow-pigmented 1–2$\mu$ thick, slightly to coarsely roughened; vesicles thick-walled, fertile over three-fourths or more of the surface, globose to subglobose, mostly 20–50$\mu$ but ranging up to 75$\mu$ in diam; sterigmata predominately biseriate, primaries mostly 6.5–12.5×3.8–6.0$\mu$ but occasionally slightly longer and swollen to near 8.2$\mu$ in diam, secondaries 5.5–11.5×2-

.1–3.4μ, rarely uniseriate 5.2–7.3×2.0–2.5μ on small vesicles; conidia globose to subglobose, yellow by transmitted light, smooth or very slightly roughened, mostly 3.0–3.3μ, rarely 3.5–4.0μ in diam, joined by tenacious connectives up to 0.5μ long. Sclerotia scattered or in concentric zones, black commonly vertically elongate with apical portion white and indeterminate in growth, mostly 2–3 mm in long axis by 1 mm wide but adjacent sclerotia often coalescing to form irregular aggregations 4 mm wide by 6 mm high or larger.

Colonies on malt agar spreading more rapidly, 7.5–8.5 cm in 10 days, lightly floccose up to 3 mm deep, plane and near Kronberg green; conidiophores more abundant than on Czapek's medium and up to 4.5 mm long; sclerotia commonly not fused, less abundant and somewhat smaller than on Czapek's medium.

*Aspergillus leporis* is clearly related to members of the *Aspergillus flavus* group as defined by Raper and Fennell (1965, The Genus Aspergillus, Williams & Wilkins, Baltimore, p 686), its only anomalous character being the yellow-pigmented conidiophore wall. It resembles *A. flavus* var. *columnaris* (Raper & Fennell) in its possession of tightly columnar conidial heads, but differs in surface color, conidiophore size and morphology, and in its production of sclerotia. The sclerotia of *A. leporis* resemble those formed in a few typical strains of *A. flavus*. *A. leporis*, *A. subolivaceus* (Raper & Fennell), and *A. avenaceus* G. Smith are similar in being predominately biseriate with ecru-olive conidial heads, and in consistently producing large, dark sclerotia; the later species differ from *A. leporis*, however, in form of the heads, conidiophore dimensions, and form and size of the conidia. *Aspergillus alliaceus* Thom & Church and certain strains of *A. tamarii* Kita also produce elongate, white-tipped sclerotia, but differ markedly from *A. leporis* in morphology and cultural characteristics.

As mentioned above, the starting material for use in this invention is the sclerotia of *A. leporis*, which has been identified as a member of the *A. flavus* taxonomic group. The sclerotia are produced by solid-substrate fermentation on corn kernels. They are prepared for extraction by grinding in a conventional manner to a suitable particle size, and then they are extracted with a nonpolar solvent, preferably hexane. The solvent extract is separated from solid material and concentrated to a light yellow oil.

Separation and purification of leporin A from the crude oil can be effected by the use of conventional techniques including, for example, countercurrent distribution (CCD), column chromatography (CC), high-performance liquid chromatography (HPLC), and thin-layer chromatography (TLC). In the preferred embodiment of the invention, we have successfully employed reversed-phase semipreparative HPLC to afford pure leporin A. While not desiring to be limited thereto, the details of the separation procedure are illustrated in Example 1.

As a practical matter, it is envisioned that commercial formulations of the subject pesticidal agent would be prepared directly from fungal extracts or fractions derived from such extracts, thereby obviating the need to isolate the compound in pure form. As indicated above, the compound is soluble in hexane; however, other suitable solvents could be readily determined by the skilled artisan. Of course, for applications demanding a high degree of specificity, that is, a high level of predictability of the intended response by both target and nontarget organisms, it would normally be preferred to prepare the formulations from pure or substantially pure leporin A. For example, it is possible that extraneous substances in the natural fungal material would have an undesirable masking or antagonistic effect with regard to the intended activity, or a toxic effect toward the nontarget species.

The potency of leporin A dictates that it be applied in conjunction with a suitable inert carrier or vehicle as known in the art. Of particular interest are those which are agronomically acceptable. Alcohols, ketones, esters, and aqueous surfactant mixtures are illustrative of suitable carriers. Depending on the substrate, target species, mode of application, and type of response desired, the concentration of active ingredient in the final composition may vary considerably, but typically should be at least about 10 ppm. Factors such as phytotoxicity toward the treated plant and tolerance of nontarget species can be used by the skilled artisan in determining the optimum level. The toxic effects of leporin A on insect species are illustrated in Example 2.

Depending on the pest species, concentration of agent, and method of application, the subject compound acts to control pests by one or more mechanisms including, for instance, death inducement, growth regulation, sterilization, as well as interference with metamorphosis and other morphogenic functions. Accordingly, the level of active agent is administered in an amount effective to induce one or more of these responses as predetermined by routine testing. Where the ultimate response is pest mortality, an "effective amount" or "pesticidally effective amount" is defined to mean those quantities of agent which will result in a significant growth inhibition or mortality rate of a test group as compared to an untreated group. The actual effective amount may vary with the species of pest, stage of larval development, the nature of the substrate, the type of vehicle or carrier, the period of treatment, and other related factors.

To be effective, the agent must be applied to the locus of, or the vicinity of, the pest to be controlled. When the agent is intended as a stomach poison, it is applied in conjunction with its carrier to the pest diet. In the case of plants, the composition will typically be applied to the leaf surfaces or else systemically incorporated. Alternatively, when the agent is to be used as contact poison, any method of topical application, such as direct spraying on the pest or on a substrate which is likely to be contacted by the pest, would be appropriate.

The compound encompassed herein is effective in controlling a variety of insects, and its toxicity is comparable to that of commercially available insecticides such as rotenone. Without desiring to be limited thereto, pests of particular interest known to be vulnerable to treatment are agronomically important insects, especially those of the order Lepidoptera, and specifically the corn earworm *Helicoverpa zea*.

The following examples are intended only to further illustrate the invention and are not intended to limit the scope of the invention which is defined by the claims.

EXAMPLE 1

Isolation and Purification of Leporin A

Sclerotia were prepared by solid-substrate fermentation of *A. leporis*, strain NRRL 18990, on autoclaved corn kernels using procedures described by Wicklow et al. [Trans. Br. Mycol. Soc. 91:433 (1988)], the contents of which are incorporated by reference herein. In review, conidia of *A. leporis* were suspended in sterile 0.01% Triton X-100 and used to inoculate whole autoclaved corn kernels forming a single layer at the bottom of Fernbach flasks. The inoculated kernels were incubated in the dark for 21 days at 28° C. Following incubation, the sclerotia were separated from the kernels by adding 250 ml of distilled water to each flask and shaking for 8 hr at 200 rev/min. The contents of each flask were passed through a 1.5 mm diameter mesh screen to remove the kernels, and free sclerotia were trapped in a No. 60 (250 μ opening) U.S.A. Standard Testing Sieve. Sclerotia were air dried and stored at 4° C. until extraction. A sample of the *A. leporis* sclerotia (67 g) was ground with a mortar and pestle and exhaustively extracted with solvent by triturating 5 times with 200-ml portions of hexane. The combined hexane extracts were filtered and evaporated to afford 279 mg of a light yellow oil. The oil was subjected to reversed-phase semipreparative HPLC (5 μ $C_{18}$ column; 250×10 mm; 90:10 methanol-water at 2.0 ml/min) yielding 11 mg of leporin A. The HPLC retention time of the compound under these conditions was 14.7 min.

Characterization of Leporin A

Leporin A is a colorless oil which has: $[\alpha]_D$ −21.9° (c 0.80; $CH_2Cl_2$); UV (MeOH) 370 (ε570), 344 (650), 283 (1750), 240 (9500); IR ($CH_2Cl_2$) 3054, 2929, 1649, 1616, 1597, 1537, 1420, 1266, 1227, 994 $cm^{-1}$; $^1H$ NMR and $^{13}C$ NMR data as shown in Table I; EIMS (70 eV) 365 ($M^+$; rel. int. 32%), 334 (100), 318 (1.1), 301 (2.0), 292 (6.9), 278 (28), 264 (24), 252 (31), 238 (46), 224 (22), 214 (17), 200 (84), 171 (50), 152 (16), 144 (13), 125 (13), 116 (21), 105 (25); HREIMS, obs. 365.1990; calcd. for $C_{23}H_{27}NO_3$, 365.1992.

The molecular formula of leporin A was established as $C_{23}H_{27}NO_3$ on the basis of HREIMS and $^{13}C$ NMR data. The UV spectrum showed absorbances characteristic of a non-indolic aromatic system, and the IR spectrum revealed that leporin A contains an amide group. The $^{13}C$ NMR spectrum indicated the presence of twelve other $sp^2$-hybridized carbons, only one of which appeared to be oxygen-substituted. One unsaturation could be accounted for by the amide functionality, and six others by olefinic or aromatic π-bonds. The remaining four unsaturations must be rings. Despite the presence of four heteroatoms, the $^1H$ NMR and DEPT data demonstrated an absence of exchangeable protons.

$^1H$ and $^{13}C$ NMR data for leporin A are provided in Table I. $^1H-^1H$ COSY data and homonuclear decoupling experiments conducted in three different solvents permitted establishment of the proton spin systems, despite extensive overlap in the upfield region of the $^1H$ NMR spectrum. Carbon-13 NMR assignments were determined through the use of selective INEPT (Bax, A., *J. Magn. Reson.* 1984, 57, 314) experiments, which afforded 2- and 3-bond C/H correlations, and by an HMQC (Bax, A.; Summers, M. F., *J. Am. Chem. Soc.* 1986, 108, 2093) experiment (Table I) which gave 1-bond C/H correlations. These data provided evidence (and carbon assignments) for the partial structure (a)

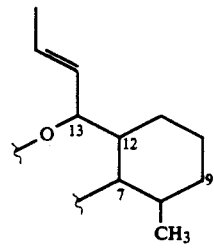

as well as a phenyl group, a methoxy group, and an isolated olefinic methine unit. Connection of the amide nitrogen to the isolated olefinic methine (C-3) was suggested by observation of a large $^1J_{CH}$ value of 180 Hz between C-3 and H-3 (Kalinkowski, H.; Berger, S.; Braun, S., *Carbon-13 NMR Spectroscopy*, Wiley: New York, 1988, 776 pp.).

The connectivity of these subunits was assigned principally on the basis of selective INEPT experiments (Table I). The olefinic proton singlet (H-3) correlated with C-17, thereby locating the phenyl group alpha to this proton. Further correlations of this proton with C-4, C-5, and C-1, in conjunction with a correlation between H-18 and C-4, indicated that the phenyl group is attached to C-4 and that H-3 is beta to both downfield $sp^2$-carbons. Observation of polarization transfer from H-7 (δ2.74) to C-5, C-6, and C-1 allowed connection of C-7 (of the partial structure) to C-6. Polarization transfer from H-13 to C-5 through the ether oxygen revealed the nature of the second connection to the partial structure and indicated the presence of a dihydropyran ring fused to the cyclohexane ring. These results also verified that the amide nitrogen must be bonded to C-3 and that leporin A contains a pyridone ring. The only remaining unit is the methoxy group, which must be attached to the amide nitrogen to give the proposed structure for leporin A. The placement of the methoxy group at this position was supported by a NOESY correlation observed between H-3 and the methoxy proton signal. Comparison of the $^{13}C$ NMR chemical shifts of leporin A with those reported for other N-alkoxypyridones (Stefaniak, L.; Witanowski, M.; Webb, G., *Bull. Acad. Pol. Sci. Ser. Sci. Chim.*, 1982, 30, 1) (Giesbrecht, A.; Gottlieb, H.; Gottlieb, O.; Goulart, M.; De Lima, R.; Sant'ana, A., *Phytochemistry*, 1980, 19, 313) also supports the structural assignment. As expected for such a structure, irradiation of the methoxy proton signal in selective INEPT experiments did not show polarization transfer to any other carbon signals, even when optimized for small J-values, and the mass spectrum shows a major ion (base peak) at M-31 (Giesbrecht, A.; Gottlieb, H.; Gottlieb, O.; Goulart, M.; De Lima, R.; Sant-'ana, A., *Phytochemistry*, 1980, 19, 313).

Despite the indications that leporin A is an N-methoxy-2-pyridone, efforts were undertaken to more rigorously exclude the possibility of an α-alkoxy N-oxide substructure. The UV spectrum did not change significantly upon acidification, and no fragment indicating the loss of 16 mass units was observed in the mass spectrum of leporin A. Further, leporin A was unreactive to conditions commonly employed to reduce pyridine N-oxides (Fe/HOAC,Zn/HOAc) (Katritzky, A. R.; Lagowski, J. M., *Chemistry of Heterocyclic N-Oxides*, Academic Press: London, 1971), and did not give a positive spot test with dimethylaniline/HCl (Coats, N. A.; Katritzky, A. R., *J. Org. Chem.*, 1959, 24, 1836).

A four-bond correlation was observed between H-3 and C-6 in a selective INEPT experiment optimized for $J_{CH}=4$ Hz (see Table I). All other correlations could be attributed to two- or three-bond relationships based on $J_{CH}$-values or other supporting data. Four-bond couplings in aromatic systems are not unusual (Kalinkowski, H.; Berger, S.; Braun, S., *Carbon-13 NMR Spectroscopy*, Wiley: New York, 1988 776 pp.), and can be detected in selective INEPT experiments optimized for small J-values (Weber, H. A.; Baenziger, N. C.; Gloer, J. B., *J. Am. Chem. Soc.*, 1990, 112, 6718). However, reports of four-bond couplings in non-aromatic systems (e.g. 2-pyridones) are relatively rare. Therefore, authentic samples of 3-methoxy-2-pyridone and N-methyl-2-pyridone were analyzed for the analogous correlation. NMR assignments were determined through analysis of selective INEPT, decoupling, and COSY data, and are in agreement with literature assignments (Vogeli, U.; von Philipsborn, W., *Org. Magn. Reson.*, 1973, 5, 551). In both model compounds, distinct four-bond correlations were observed between H-6 and C-3 in experiments optimized for 4 Hz.

Despite the overlap of certain key signals in the $^1$H NMR spectrum, the relative stereochemistry shown for leporin A could be assigned on the basis of $^1$H—$^1$H coupling constants and a NOESY experiment. The propenyl group was assigned the E-geometry due to the coupling constant between the vinyl protons (15.4 Hz). The small coupling between H-7 and H-12 (3.9 Hz) is indicative of a cis-ring fusion. A trans-diaxial coupling (10.8 Hz) was observed between H-7 and H-8, suggesting that the methyl group (C-23) is equatorial and cis to H-7. An 11.2 Hz coupling between H-12 and H-13 also suggests a trans-diaxial-type relationship between these two protons, which would place the propenyl substituent in a pseudoequatorial position. Further conformational details could not be determined from the NOESY data due to signal overlap, but these data, plus a NOESY correlation between the C-24 methoxy protons and the methyl protons on C-23, are consistent with the adoption of a chair conformation by the cyclohexane portion of the molecule.

EXAMPLE 2

Insecticidal Activity of Leporin A

The compound was evaluated by insect bioassays described previously in Dowd [Entomol. Exp. Appl. 47: 69 (1988) and U.S. Pat. No. 5,017,598], the contents of each of which are incorporated by reference herein. Neonate larvae of *H. zea* and second instar (ca. 0.75 mg) larvae of *C. hemipterus* were used for all assays. They were obtained from laboratory colonies reared on pinto bean-based diet at 27°±1° C., 40±10% relative humidity, and a 14:10 light:darl photoperiod.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. The leporin A was added in 125 μl of acetone to the liquid diet to give a final concentration of 100 ppm. Upon addition of the leporin A, the mixture was removed from the water bath. The chemical was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate *H. zea* or 5 *C. hemipterus* larvae [Wicklow et al., supra (1988)] was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2, 4, and 7 days, and the surviving larvae were weighed after 7 days. Each chemical set was tested on a total of 40 larvae. Diet feeding rating for *C. hemipterus* larvae was based on a scale of 1 (limited to no feeding) to 4 (diet thoroughly tunneled or pulverized [Wicklow et al., supra (1988)].

Leporin A exhibited moderate activity against the widespread crop pest, corn earworm (*Heliothis zea*), where it caused 35.6% reduction in growth weight of insects surviving for 7 days relative to controls, when incorporated into a standard diet at 100 ppm. It did not cause any significant reduction in growth of dried-fruit beetle larvae, *Carpophilus hemipterus*, at the dosage tested.

It is understood that the foregoing detailed description is given merely by way of illustration and that modification and variations may be made therein without departing from the spirit and scope of the invention.

TABLE 1

| | Proton and Carbon 13 NMR Data for Leporin A[a] | | |
|---|---|---|---|
| H/C# | $^1$H | $^{13}$C[c] | Sel INEPT[b] Correlations |
| 1 | — | 158.56 | |
| 2 | — | — | |
| 3 | 7.58 (s) | 133.18 | 1, 4[e], 5, 6[d], [e], 17 |
| 4 | — | 113.60 | |
| 5 | — | 158.18 | |
| 6 | — | 113.44 | |
| 7 | 2.74 (dd; 3.9, 10.8) | 38.65 | 1, 5, 6, 8, 12, 13 |
| 8 | 1.65 (m) | 36.72 | |
| 9 | 1.31 (m), 1.23 (m) | 36.18 | |
| 10 | 1.51 (m), 1.78 (m) | 21.45[f] | |
| 11 | 1.57 (m), 1.80 (m) | 27.26[f] | |
| 12 | 1.71 (m) | 36.66 | |
| 13 | 4.88 (dd; 8.3, 11.2) | 78.48 | 5[e], 7[e], 12, 14, 15 |
| 14 | 5.42 (ddq; 1.7, 8.3, 15.4) | 130.64 | 12[e], 13[e], 16 |
| 15 | 5.81 (dq; 6.4, 15.4) | 131.41 | 13, 16 |
| 16 | 1.68 (dd; 1.7, 6.6) | 17.86 | 14, 15 |
| 17 | — | 135.10 | |
| 18/22 | 7.46 (br d; 7.3) | 130.00 | 4, 19, 20, 18/22 |
| 19/21 | 7.32 (br dd; 7.3, 7.3) | 128.78 | 17, 18/22, 19/21, 20 |

TABLE 1-continued

Proton and Carbon 13 NMR Data for Leporin A[a]

| H/C# | [1]H | [13]C[c] | Sel INEPT[b] Correlations |
|---|---|---|---|
| 20 | 7.26 (br t; 7.3) | 127.75 | 18/22, 19/21 |
| 23 | 0.93 (d; 6.3) | 21.16 | 7, 8, 9 |
| 24 | 4.00 (s) | 64.59 | None |

[a]Data were recorded in acetone-d6 at 360 and 90.7 MHz, respectively.
[b]Proton signals studied with the selective INEPT technique were individually subjected to several separate experiments, optimizing for 2, 4, 7, 10, or 12 Hz.
[c]Carbon multiplicities were established by a DEPT experiment, and are consistent with the assignments.
[d]Denotes a four-bond correlation.
[e]These correlations were observed only in experiments optimized for 4 Hz or less.
[f]These assignments may be interchanged.

We claim:

1. A substantially pure N-methoxy-2-pyridone designated leporin A and having the structure:

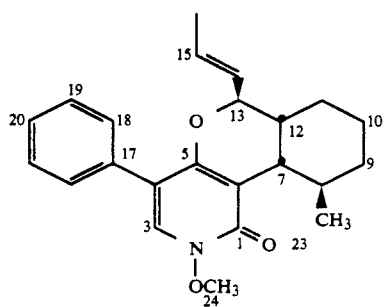

and wherein said leporin A is free of cells and sclerotia of *Aspergillus leporis*.

2. A composition for controlling insects comprising an insecticidally effective amount of leporin A having the structure:

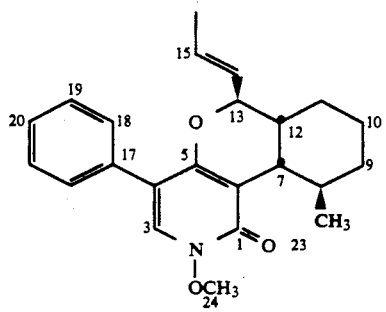

and an inert carrier.

3. A method for controlling insects comprising applying to a locus of said insects an insecticidally effective amount of leporin A having the structure:

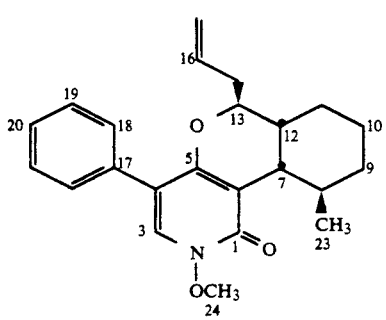

4. The method as described in claim 3 wherein said insects are Lepidoptera species.

5. The method as described in claim 3 wherein said insects are *Heliothis zea*.

* * * * *